US008929629B1

(12) United States Patent
Rozenfeld

(10) Patent No.: US 8,929,629 B1
(45) Date of Patent: *Jan. 6, 2015

(54) METHOD AND SYSTEM FOR IMAGE-BASED ULCER DETECTION

(71) Applicant: Given Imaging Ltd., Yoqneam (IL)

(72) Inventor: Stas Rozenfeld, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/262,078

(22) Filed: Apr. 25, 2014

Related U.S. Application Data

(63) Continuation of application No. 13/537,278, filed on Jun. 29, 2012, now abandoned.

(60) Provisional application No. 61/502,465, filed on Jun. 29, 2011.

(51) Int. Cl.
G06K 9/00 (2006.01)
G06T 7/00 (2006.01)
A61B 5/00 (2006.01)
G06K 9/62 (2006.01)

(52) U.S. Cl.
CPC ............ *G06K 9/6256* (2013.01); *G06T 7/0012* (2013.01); *A61B 5/7275* (2013.01)
USPC ........................................................ 382/128

(58) Field of Classification Search
None
See application file for complete search history.

(56) References Cited

U.S. PATENT DOCUMENTS

| 4,278,077 | A | 7/1981 | Mizumoto |
| 4,936,823 | A | 6/1990 | Colvin et al. |
| 5,212,637 | A | 5/1993 | Saxena |
| 5,604,531 | A | 2/1997 | Iddan et al. |
| 5,697,384 | A | 12/1997 | Miyawaki et al. |
| 5,993,378 | A | 11/1999 | Lemelson |
| 6,240,312 | B1 | 5/2001 | Alfano et al. |
| 7,009,634 | B2 | 3/2006 | Iddan et al. |
| 7,567,692 | B2 | 7/2009 | Buzaglo et al. |
| 7,684,599 | B2 | 3/2010 | Horn et al. |
| 8,423,123 | B2 | 4/2013 | Horn |
| 2002/0103417 | A1 | 8/2002 | Gazdinski |
| 2002/0177779 | A1* | 11/2002 | Adler et al. ................... 600/476 |
| 2003/0167000 | A1 | 9/2003 | Mullick et al. |
| 2003/0208107 | A1 | 11/2003 | Refael |
| 2003/0223627 | A1 | 12/2003 | Yoshida et al. |
| 2004/0225223 | A1 | 11/2004 | Honda et al. |
| 2005/0152588 | A1 | 7/2005 | Yoshida et al. |

(Continued)

OTHER PUBLICATIONS

Office action of U.S. Appl. No. 13/537,278 mailed Sep. 30, 2013.

(Continued)

*Primary Examiner* — Stephen R Koziol
*Assistant Examiner* — Raphael Schwartz
(74) *Attorney, Agent, or Firm* — Pearl Cohen Zedek Latzer Baratz LLP

(57) ABSTRACT

A system and method for ulcer detection which may generate a vector of grades including grades indicative of a probability that the image includes an ulcer, for example an ulcer of specific type. For each grade, generating may include finding ulcer candidates within the image, and for each ulcer candidate, building a property vector describing properties of the ulcer candidate and employing a trained classifier to generate the grade from the property vector. The grades may be combined to obtain an indication or score of the probability that the image includes an ulcer.

19 Claims, 9 Drawing Sheets

(56) References Cited

U.S. PATENT DOCUMENTS

| | | |
|---|---|---|
| 2005/0192476 A1* | 9/2005 | Homan et al. ............... 600/118 |
| 2005/0259854 A1 | 11/2005 | Arimura et al. |
| 2006/0069317 A1 | 3/2006 | Horn et al. |
| 2007/0078300 A1 | 4/2007 | Zinaty et al. |
| 2007/0078335 A1 | 4/2007 | Horn |
| 2010/0046816 A1 | 2/2010 | Igual-Munoz et al. |
| 2010/0183210 A1 | 7/2010 | Van Uitert et al. |
| 2010/0189326 A1 | 7/2010 | McGinnis et al. |
| 2011/0033094 A1 | 2/2011 | Zarkh et al. |
| 2011/0206250 A1 | 8/2011 | McGinnis et al. |
| 2012/0008838 A1 | 1/2012 | Guyon et al. |

OTHER PUBLICATIONS

Notice of Allowance U.S. Appl. No. 13/537,278 mailed Jan. 27, 2014.
Office Action of U.S. Appl. No. 13/441,130 mailed Mar. 13, 2014.
Notice of Allowance of U.S. Appl. No. 13/441,130 mailed Jun. 24, 2014.
U.S. Appl. No. 13/441,130 submitted Apr. 6, 2012.

* cited by examiner

METHOD AND SYSTEM FOR IMAGE-BASED ULCER DETECTION

PRIOR APPLICATION DATA

The present application is a continuation application of U.S. patent application Ser. No. 13/537,278, filed Jun. 29, 2012, which claims benefit from prior U.S. provisional application Ser. No. 61/502,465, filed Jun. 29, 2011, and entitled "METHOD AND SYSTEM FOR IMAGE-BASED ULCER DETECTION", incorporated herein by reference in their entirety.

FIELD OF THE INVENTION

Embodiments of the present invention relate to systems and methods for ulcer detection. More specifically, embodiments of the present invention relate to systems and methods for automatically detecting ulcers within image frames captured by an in-vivo device traveling in the gastrointestinal (GI) tract.

BACKGROUND OF THE INVENTION

Mucosal erosions in the walls of the GI tract, typically referred to as ulcers or peptic ulcers, are a painful disease of the GI tract. Ulcers may occur in the stomach, doudenum and esophagus, etc.

Ulcers may be diagnosed based on characteristic symptoms such as abdominal pain, or using tests such as endoscopies or barium contrast x-rays. For example, gastroscopy may provide direct visual identification of the ulcer, including information relating to the location and severity of the ulcer. Alternatively, a swallowable in-vivo device, such as the PillCam® capsule endoscopy system commercially available from the common assignee of the present invention or an autonomous swallowable imaging device similar to embodiments described in U.S. Pat. No. 7,009,634 and/or in U.S. Pat. No. 5,604,531, each of which are assigned to the common assignee of the present invention and each of which are hereby incorporated by reference in their entirety, may travel along the GI tract, capture images of the GI tract, and send these images to a personal computer or workstation or portable recorder to be analyzed and presented to a healthcare professional. The healthcare professional may diagnose the presence of ulcers based on the captured images.

A capsule endoscope video may comprise of tens of thousands of images captured during the capsule's several hours' long passage through the GI tract. Often time, the vast majority of images in such image stream are of healthy tissue and a much smaller number of images show pathological tissue, such that the reviewer may need a long time to locate images of diagnostic interest. An automatic detection of images showing pathological tissue, such as an ulcer, may save reviewing time and increase the likelihood of detection of such pathological tissue by the reviewer.

Ulcers in the GI tract may have unique visual appearance. Typically, peptic ulcers are characterized by a white-yellowish center surrounded by a reddish halo.

SUMMARY OF THE INVENTION

According to embodiments of the invention there is provided a system and method for ulcer detection which may generate a vector of grades or ratings including grades indicative of a probability that the image includes an ulcer (e.g., an ulcer is depicted or portrayed in the image, or that the image includes an image of an ulcer), for example an ulcer of specific type. For each grade generating may include finding or generating ulcer candidates within the image, and for each ulcer candidate, building or creating a property vector or other property list describing properties of the ulcer candidate and employing or using a trained classifier to generate the grade from the property vector. The grades may be combined to obtain or generate an indication of the probability that the image includes an ulcer.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
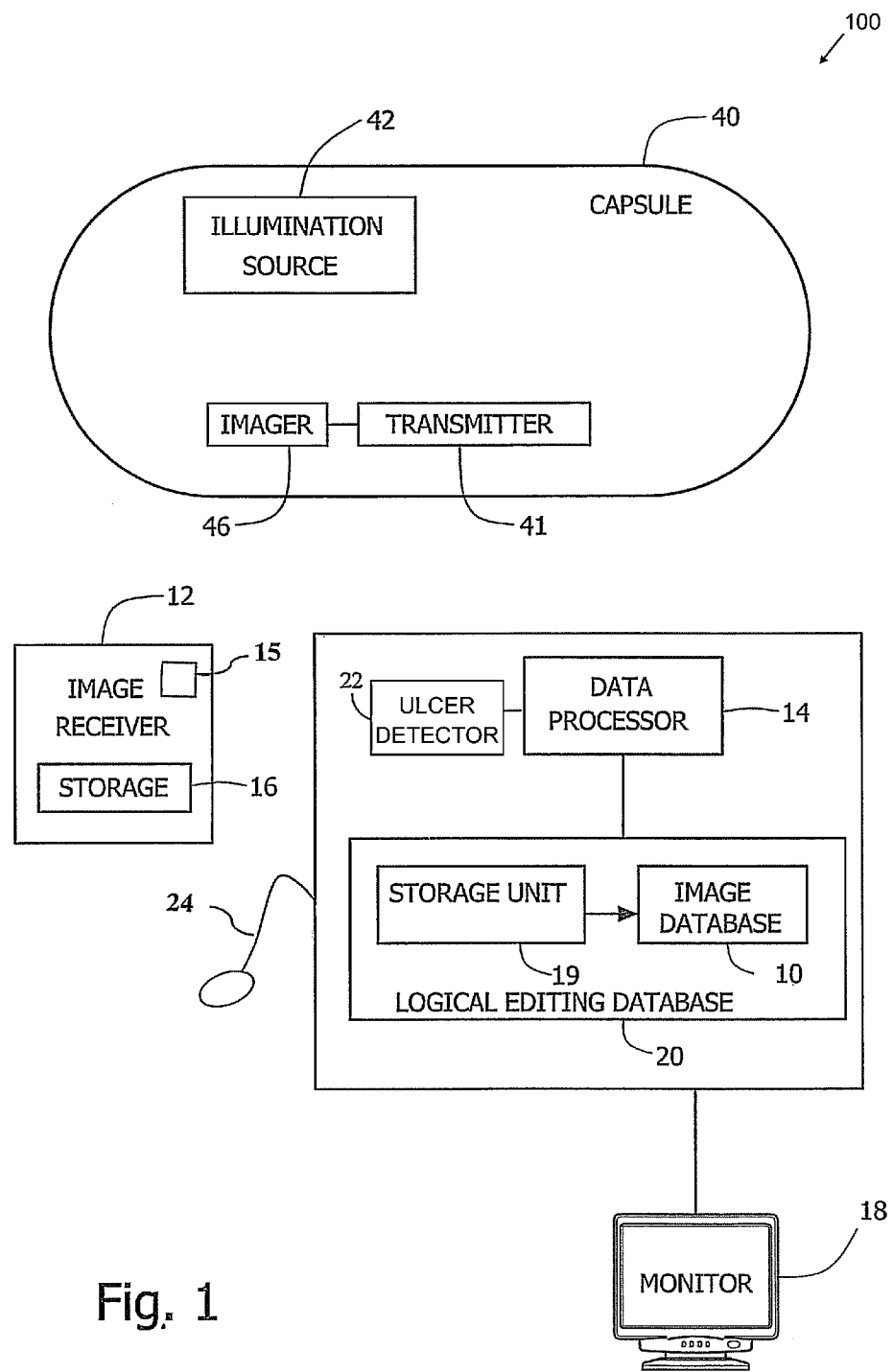
FIG. 1 schematically illustrates an in-vivo imaging system according to embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although embodiments of the present invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

Although embodiments of the present invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed at the same point in time.

Some embodiments of the present invention are directed to a typically swallowable in-vivo device, such as an autonomous swallowable imaging device. Other embodiments need not be swallowable or autonomous, and may have other shapes or configurations. Devices according to embodiments of the present invention, including imaging, receiving, processing, storage and/or display units suitable for use with embodiments of the present invention, may be similar to the PillCam® capsule endoscopy system commercially available from the common assignee of the present invention or to embodiments described in U.S. Pat. No. 7,009,634 and/or in U.S. Pat. No. 5,604,531, each of which are assigned to the common assignee of the present invention and each of which are hereby incorporated by reference in their entirety. Of course, devices and systems as described herein may have other configurations and other sets of components.

Reference is made to FIG. 1, which schematically illustrates an in-vivo imaging system 100 according to embodiments of the present invention.

According to some embodiments, system 100 may include an imaging device 40 for autonomously traveling and capturing images in-vivo. Device 40 may be a swallowable in-vivo capsule, but other sorts of devices or suitable implementations may be used. According to one embodiment, device 40 may communicate with an external receiving and display system to provide display of data, control, or other functions. Power may be provided by an internal battery or a wireless receiving system. Other embodiments may have other configurations and capabilities.

Device 40 may include an imager 46, for capturing images, an illumination source 42, for illuminating the body lumen, and a transmitter 41, for transmitting image and possibly other information to a receiving device. Transmitter 41 may include receiver capability, for example, to receive control information. An optical system, including, for example, lenses or mirrors, may aid in focusing reflected light onto the imager 46.

Preferably, located outside the patient's body in one or more locations, are an image receiver 12, preferably including an antenna or antenna array, an image receiver storage unit 16, and a data processor 15, a data processor 14, a data processor storage unit 19, and an image monitor 18, for displaying, for example, the images recorded by device 40. Preferably, the image receiver 12 and image receiver storage unit 16 are small and portable, and are worn on the patient's body during recording of the images.

According to embodiments of the present invention, data processor storage unit 19 may include an image database 10 and a logical editing database 20. In some embodiments, logical editing database 20 may be integrated into storage unit 19 or need not be used. According to one embodiment, logical editing database 20 may include criteria for editing a moving image steam, for example, including rules and logic for determining the probability that selected images stored in the image database 10 may include an ulcer (e.g., that the images include sub-portions which are images of ulcers). Data processor storage unit 19, and storage unit 16, may also store code or instructions such as software which, when executed by a processor, perform methods as disclosed herein.

Storage units 19 and image database 10 may store data such as image frames, image streams, and edited image streams and data describing the probability that an image includes an ulcer (e.g., the probability or likelihood that the images depict ulcers).

According to one embodiment of the present invention, data processor 14, data processor storage unit 19 and monitor 18 are part of a personal computer or workstation which includes standard components such as a processor, a memory, a disk drive, and input-output devices, although alternate configurations are possible, and the system and method of the present invention may be implemented on various suitable computing systems. An input device 24 may receive input from a user (e.g., via a pointing device, click-wheel or mouse, keys, touch screen, recorder/microphone, other input components) and send corresponding commands to trigger control of the computer components, e.g., data processor 14.

Data processor 14 or 15 may include any standard data processor, such as a microprocessor, multiprocessor, accelerator board, or any other serial or parallel high performance data processor. Image monitor 18 may be a computer screen, a conventional video display, or any other device capable of providing image or other data.

Imager 46 may be a complementary metal-oxide-semiconductor (CMOS) camera, such as a "camera on a chip" type CMOS imager specified by Given Imaging Ltd. of Israel and designed by Aptina Corporation of California, USA. In alternate embodiments, the imager 46 may be another device, for example, a charge-coupled device (CCD). The illumination source 42 may be, for example, one or more light emitting diodes, or another suitable light source.

In operation, imager 46 may capture images and send data representing the images to transmitter 41, which transmits images to image receiver 12 using, for example, electromagnetic radio waves. Image receiver 12 may transfer the image data to image receiver storage unit 16. After a certain period of time of data collection, the image data stored in storage unit 16 may be sent to the data processor 14 or 15 or the data processor storage unit 19 or 16, respectively. For example, the image receiver storage unit 16 may be taken off the patient's body and connected to the personal computer or workstation which includes the data processor 14 and data processor storage unit 19 via a standard data link, e.g., a serial or parallel interface of known construction. The image data may then be transferred from the image receiver storage unit 16 to the image database 10 within data processor storage unit 19.

Data processor storage unit 19 may store a series of images recorded by device 40. The images the device 40 records as it moves through a patient's GI tract may be combined consecutively to form a moving image stream.

Data processor 14 may analyze and edit the moving image stream, for example, according to the logical editing database 20, and provide the analyzed and edited data to the image monitor 18, where for example a health professional views the image data. Data processor 14 may operate software which, in conjunction with basic operating software such as an operating system and device drivers, controls the operation of data processor 14. According to one embodiment, the software controlling data processor 14 may include code written, for example, in the C++ language and possibly alternative or additional languages, and may be implemented in a variety of known methods. Alternatively, data processor 15 may analyze and edit the moving image stream.

The image data collected and stored may be stored indefinitely, transferred to other locations, or manipulated or analyzed. A health professional may use the images to diagnose pathological conditions of for example the GI tract, such as ulcers, and, in addition, the system may provide information about the location of these pathologies. While using a system where the data processor storage unit 19 or 16 first collects data and then transfers data to the data processor 14 or 15, respectively, the image data is not viewed in real time, however, other configurations allow for real time viewing.

According to one embodiment, the device 40 may collect a series of still images as it traverses the GI tract. The images may be later presented as, for example, a stream of images or a moving image of the traverse of the GI tract. The in-vivo imager system may collect a large volume of data, as the device 40 may take several hours to traverse the GI tract. The imager 46 may record images at a rate of, for example, four to forty images per second (other rates, such as two frames per second, may be used). The imager 46 may have a fixed or variable frame capture and/or transmission rate. When the imager 46 has a variable or adaptive frame rate (AFR), the imager 46 may switch back and forth between frame rates, for example, based on parameters, such as the device 40 speed, forward or reverse direction, estimated location, similarity between consecutive images, or other criteria.

Preferably, the image data recorded and transmitted by device 40 is digital color image data, although in alternate embodiments other image formats may be used. In an exemplary embodiment, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (RGB, where one primary is represented twice). The brightness of the overall pixel may be recorded by a one byte (i.e., 0-255) brightness value. Alternatively, in each pixel, data may be represented by cylindrical-coordinate representation formats such as hue, saturation and lightness (HSL or HLS), hue, saturation and value or brightness (HSV or HSB), or hue, saturation and intensity (HIS). Cylindrical-coordinate representations of the RGB color space are characterized by representing the color or hue information by the angle around a central vertical axis while the distance from the axis corresponds and the distance along the axis corresponds to other information such as saturation and brightness. For example, when using HSV representation, a hue (H) value may represent the angle around the central vertical axis a saturation (S) value may represent the distance from the axis, and a value (V) may represent the distance along the axis. Alternatively, other representations may be used, such as YCbCr (Y is the luma or luminance component and Cb and Cr are the blue-difference and red-difference chroma components), Lab color space etc. According to one embodiment, images may be stored for example sequentially in data processor storage unit 19. The stored data may include one or more pixel properties, including H, S and V.

According to an embodiment of the present invention, the data processor 14 may include or function as an ulcer detector 22 for detecting ulcers in images of the moving image stream. Other data processors in other devices may function as an ulcer detector.

Ulcer detector 22 (and other modules, classifiers, integrators and processes discussed herein) may be a dedicated processor (e.g., an ulcer detector processor) or may be implemented by data processor 14 or 15 (e.g., may be software or code stored in a memory such as storage 16 or 19 and executed by a processor). While the ulcer detector 22 is shown in FIG. 1 as being separate from and connected to processor 14, in some embodiments ulcer detector 22 may be a set of code or instructions executed by processor 14 or 15 (e.g., may be processor 14 or 15). Ulcer detector 22 may be or include one or more dedicated processors.

While preferably, information gathering, storage, and processing are performed by certain units, the system and method of the present invention may be practiced with alternate configurations. For example, the components gathering image information need not be contained in a capsule, but may be contained in any other vehicle suitable for traversing a lumen in a human body, such as an endoscope, stent, catheter, needle, etc.

Figure 2:
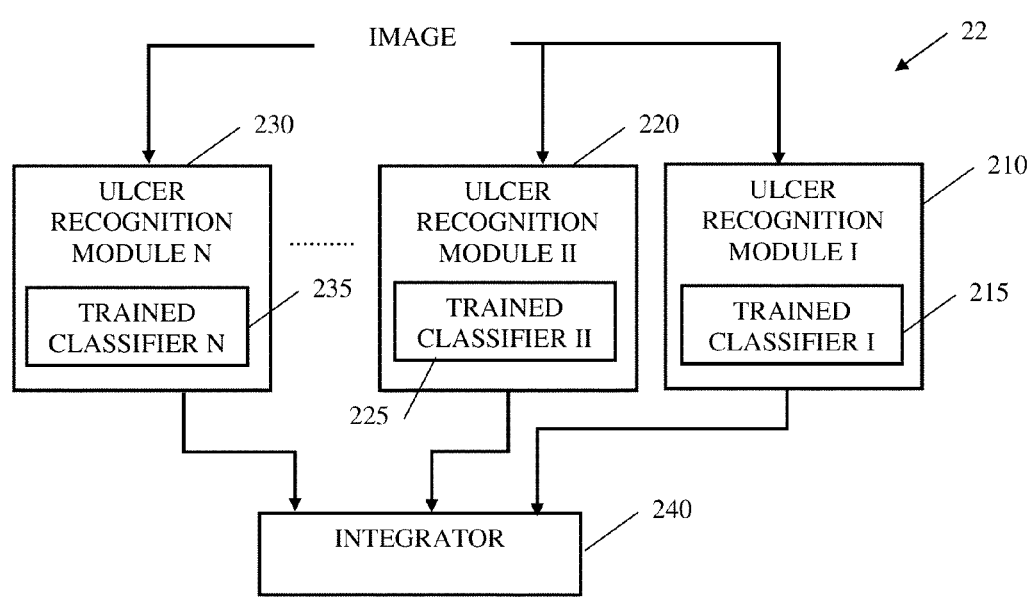
FIG. 2 is a schematic diagram illustrating an exemplary ulcer detector according to embodiments of the present invention.

Reference is made to FIG. 2, which is a schematic diagram illustrating an exemplary ulcer detector 22 according to embodiments of the present invention. According to embodiments of the present invention, ulcer detector 22 may include a plurality of ulcer recognition modules 210, 220 and 230, and an integrator or combiner 240.

Ulcer recognition modules 210, 220 and 230 may each obtain images, for example, images of the GI tract captured in vivo by imaging device 40, and may produce a rating or grade or rating indicative of a probability that the image includes an ulcer. A grade may be, for example, a number in a range, a percentage, one of a number of discrete categories, etc. For example, the grade or rating may indicate that the image may contain or depict an ulcer of a specific type. Alternatively, ulcer recognition modules 210, 220 and 230 may each produce a plurality of ratings or grades for an image, each indicative of a probability that an ulcer candidate found in the image is an ulcer. Throughout the specification, an ulcer type may refer to a group of ulcers having a typical visual appearance. For example, an ulcer type may include ulcers having a specific range of center color, halo color, center size or geometry etc. Throughout the specification, a size of an element presented in an image refers to the number of pixels of that element. Alternatively, other measures of sizes may be used. For example, when using HSV representation, in which the full range of H is [0;1], the full range of S is [0;1] and a full range of V is [0;255], an exemplary ulcer type may be specified by having center color in the range of $4456/65535 < H < 5702/65535$, $39321/65535 < S < 47841/65535$ and $80 <= V <= 255$, halo color in the range of $0 < H < 3604/65535$, $37355/65535 < S < 1$ and $80 <= V <= 255$, and center size in the range of 21 to 2000 pixels. Other ulcer types may have other ranges of colors and sizes.

Ulcer recognition modules 210, 220 and 230 may each include a classifier such as trained classifier 215, 225 and 235, respectively. The trained classifiers 215, 225 and 235 may produce a grade or rating for each ulcer candidate based on for example property vector or other property list built or created for that ulcer candidate. Trained classifiers 215, 225 and 235 may be classifiers trained by supervised learning methods such as neural network classifiers, Fisher linear discriminant classifiers, sparse network of Winnows classifiers, decision tree classifiers, Bayes classifiers, support vector machines, AdaBoost classifiers, etc. Alternatively, other learning techniques and/or classifiers may be used.

Integrator or combiner 240 may receive the ratings or grades produced by the plurality of ulcer recognition modules 210, 220 and 230 (for example, the grades may be organized in a vector of grades or ratings), and may combine or otherwise use these grades to obtain or generate a single indication or rating of the probability that the image includes an ulcer or that an ulcer candidate is an ulcer. While a specific set of modules (classifiers, and integrator, etc.) are described, the functionality described herein may be carried out by other combinations of modules.

Figure 3:
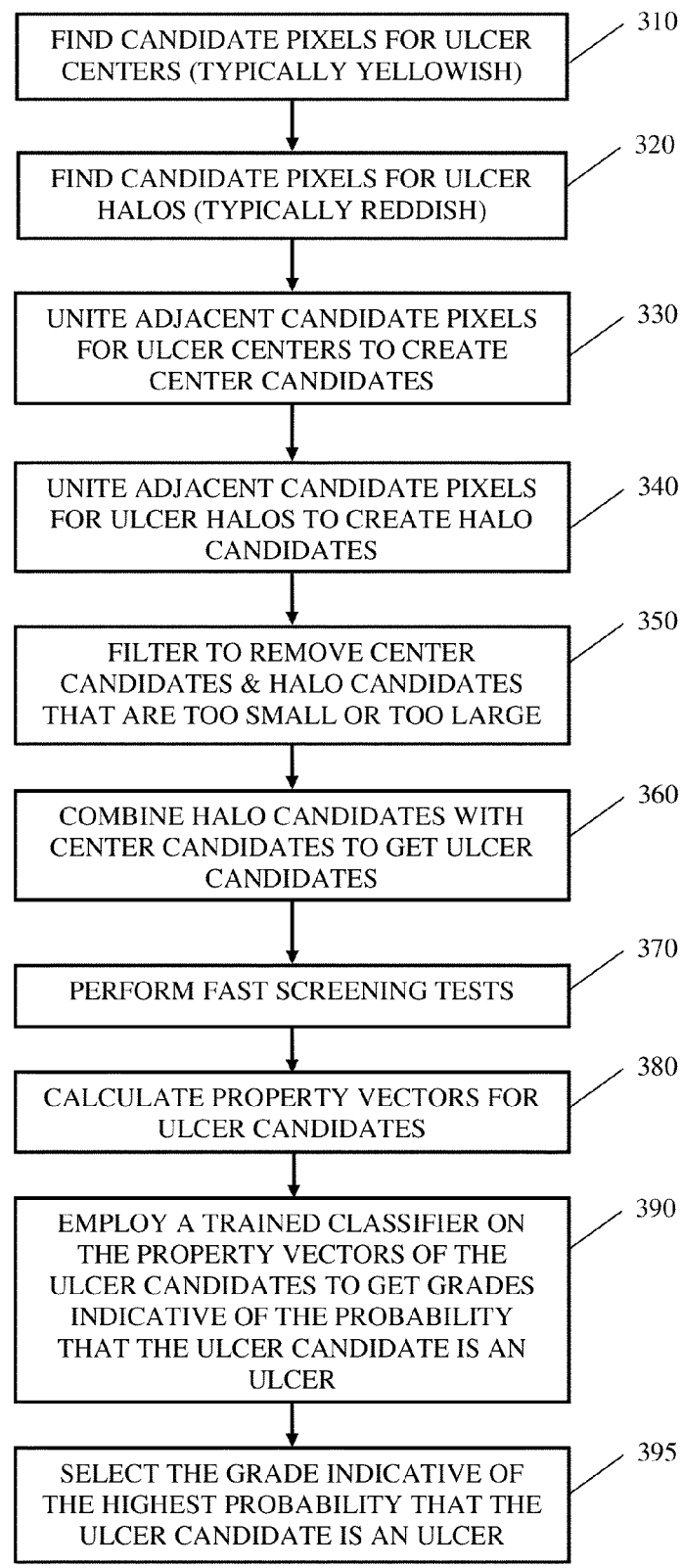
FIG. 3 is a flowchart illustration of a method for ulcer recognition according to embodiments of the present invention.

Reference is now made to FIG. 3, a flowchart illustration of a method for ulcer recognition according to embodiments of the present invention. For example, the method for ulcer recognition presented in FIG. 3 may be performed by ulcer recognition modules 210, 220 and 230. Other numbers of detector modules may be used.

According to embodiments of the present invention, candidate pixels, e.g. within images of the GI tract obtained from imaging device 40, for ulcer centers may be found in operation 310. For example, pixels having a color within a predetermined range may be noted or marked as candidate pixels for ulcer centers. Pixels may be marked by any applicable method, as know in the art. For example, metadata may be added to the image. Typically, ulcer centers are of white-yellowish color. However centers of different types of ulcers may have different shades of white or yellow. Therefore, different ranges may be used by different ulcer recognition modules 210, 220 and 230 to detect candidate pixels for ulcer centers of different types of ulcers. In operation 320 candidate pixels for ulcer halos may be found. For example, pixels having a color within a predetermined range may be noted or marked as candidate pixels for ulcer halos. Typically, ulcer halos are of reddish color. However halos of different types of ulcers may have different shades of red. Therefore, different ranges may be used by different ulcer recognition modules 210, 220 and 230 to detect candidate pixels for ulcer halos of different types of ulcers.

In operation 330 adjacent or nearby candidate pixels or groups of pixels for ulcer centers may be combined or united (e.g., in a virtual manner, for example, using metadata) to create ulcer center candidates and in operation 340 adjacent or nearby candidate pixels or groups of pixels for ulcer halos may be combined or united to create ulcer halo candidates. In operation 350 ulcer center candidates and ulcer halo candidates that are too small or too large may be filtered (e.g., filtered out) to be removed. For example, threshold levels may be determined for filtering out ulcer center candidates that are below a predetermined size or above a predetermined size. Similarly, threshold levels may be determined for filtering out ulcer halo candidates that are below a predetermined size or above a predetermined size. As ulcer types may differ in size and geometry of their centers and halos, threshold levels used for filtering (e.g., removing) ulcer center candidates and ulcer halo candidates may differ between the different ulcer detector modules 210, 220 and 230.

In operation 360, ulcer candidates may be determined. For example, ulcer center candidates and ulcer halo candidates may be combined to create or generate ulcer candidates or regions possibly being an image of an ulcer. According to embodiments of the present invention, ulcer center candidates and ulcer halo candidates may be combined by forming (e.g., in a virtual manner, for example, using metadata) a ring or other boundary around an ulcer center candidate. For example the ring may be created by using a morphological opening operation followed by removing the pixels of the ulcer center candidate itself. An ulcer candidate or a region possibly being an image of an ulcer may be created or defined by combining an ulcer center candidate with the pixels of halo candidates that fall within the ring of that ulcer center candidate.

The ranges for detecting candidate pixels for ulcer centers and candidate pixels for ulcer halos, as well as threshold levels for filtering out (e.g., removing) ulcer center candidates and ulcer halo candidates that are too small or too large, and various threshold levels a ranges used to filter out (e.g., removing) ulcer candidates, for the different ulcer detector modules 210, 220 and 230, may be determined manually by viewing exemplary images containing the various types of ulcers, automatically, by pre-set values, by trial and error or by any other suitable method.

Figure 4:
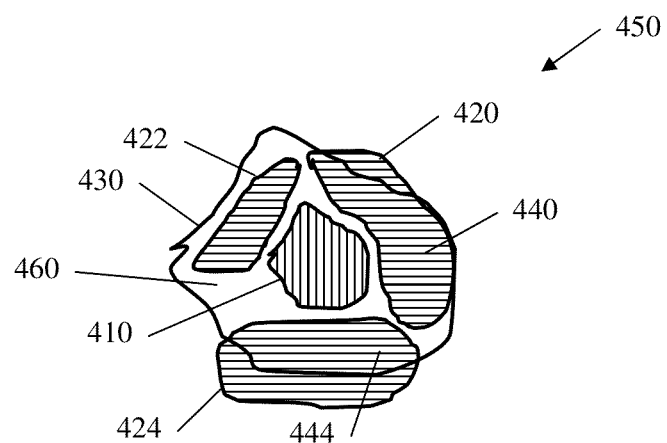
FIG. 4. is a schematic diagram illustrating an exemplary ulcer candidate according to embodiments of the present invention.

Reference is now made to FIG. 4, a schematic diagram illustrating an exemplary ulcer candidate according to embodiments of the present invention. An ulcer candidate may be a region, set of regions, or areas in an image which have been identified as possibly depicting or capturing an ulcer. A ring or other boundary 430 may be formed around ulcer center candidate 410. Ring 430 defines ring area 460 between ring 430 and ulcer center candidate 410. Ulcer halo candidate 422 falls within ring 430 while ulcer halo candidates 420 and 424 partially fall within ring 430. Ulcer center candidate 410 may therefore be combined, for example, with ulcer halo candidates 422 and part of ulcer halo candidates 420 and 424 that fall within the ring (i.e. 440 and 444 respectively) to form a single ulcer candidate 450 or a region possibly depicting or capturing an ulcer. The total area of ulcer halo candidates that is included within ring area 460 may be referred to as an intersection area. For example, the intersection area of ulcer candidate 450 may include area 440 which is the part of ulcer halo candidate 420 that falls within ring 430, area 444 which is the part of ulcer halo candidate 424 that falls within ring 430, and the area of ulcer halo candidate 422 which fully falls within ring 430.

Returning to FIG. 3, in operation 370 fast screening tests may be performed to filter out (e.g., removing) ulcer candidates. The fast screening tests may include, for example:

filtering to remove ulcer candidates for which the size of the corresponding ring or boundary area is above a predetermined threshold.

filtering to remove ulcer candidates for which the size of the corresponding intersection area is below a predetermined threshold, filtering to remove ulcer candidates for which the size of the corresponding intersection area divided by the size of the corresponding ring area is below a predetermined threshold, filtering to remove the ulcer candidates for which square of the circumference of the ulcer center candidate divided by the size of the ulcer center candidate is above a predetermined threshold (e.g., circumference of the ulcer center candidate may be measured by identifying the pixels positioned on the boundary of the ulcer center candidate, and accumulating distances between adjacent pixels), filtering to remove the ulcer candidates for which the difference between an average color of the ulcer center candidate and an average color of the corresponding intersection area is outside a predetermined range, and filtering to remove ulcer candidates for which a largest part of the corresponding ring area that pertain to a single ulcer halo candidate is above a predetermined threshold. Ulcer detector modules 210, 220 and 230 may each employ or use none, some or all of the above listed fast screening tests, or other tests. Similarly, threshold levels and ranges may differ among ulcer detector modules 210, 220 and 230.

According to some embodiments of the present invention, the fast screening tests may be performed sequentially, such that each ulcer candidate that fails in one of the fast screening tests is removed and does not undergo the remaining tests. In addition, the fast screening tests may be ordered substantially according to their computational complexity such that fast screening tests with relatively low complexity, such as fast screening tests that relate to color differences are performed before the fast screening test with relatively high complexity, such as fast screening tests that involve calculation of the circumference.

In operation 380 a property vector or other list may be calculated, created or built for ulcer candidates or regions possibly depicting an image of an ulcer that were not removed. Throughout the application the term vector may relate to an ordered list of parameters, ratings, or other numbers or data items. For example, the property vector or other list may include or be an ordered list of data structure including various parameters describing properties of the ulcer candidate, such as parameters related to the color, size and shape of the ulcer candidates including centers, rings and halos of the ulcer candidates. For example, the property vector of each ulcer detector modules 210, 220 and 230 may include some or all of the parameters listed in table 1. Other parameters, similar to these presented in table 1 may be used as well. Some of the parameters in table 1 are presented with relation to HSV cylindrical-coordinate color scheme representation format; however, similar or equivalent parameters may be defined for other image representation formats. It should be noted that the same parameters may have different values in different ulcer detector modules 210, 220 and 230, since each of ulcer detector modules 210, 220 and 230 may use different threshold levels as described hereinabove.

Various pixel parameters may be extracted or derived from pixel data captured by a digital imager, according to embodiments of the present invention. For example, chroma-related pixel values may be extracted, and may be related to the hue or wavelength of the captured pixel. Intensity-related parameters indicate an overall intensity or strength of the light (or illumination) captured in the pixel. Saturation-related parameters may be extracted or derived and may refer to the dominance of hue in the color, or the purity of the color. Saturation may indicate the ratio of the dominant wavelength to other wavelengths in the color represented by a pixel. It is noted that the H (Hue), S (Saturation) and V (Value) values listed in Table 1 are part of the HSV color space representation. Other color spaces (or color models) may be used, e.g. RGB, HSL, HSB, CIE XYZ, CIELUV, CIELAB, CMYK, YUV, YCbCr, etc.

TABLE 1

Sample parameters for property vectors or lists.

| Abbreviation | Description |
| --- | --- |
| Hc; | Average chroma-related value of pixels pertaining to a center of an ulcer candidate (e.g., average H value). |
| Sc; | Average saturation-related value of pixels pertaining to a center of an ulcer candidate (e.g., average S value). |
| Vc; | average intensity-related value of pixels pertaining to a center of an ulcer candidate (e.g., average V value in HSV color space, or average R (red) values of the pixels pertaining to a center of an ulcer candidate in an RGB color space) |
| Hr; | Average chroma-related value of pixels pertaining to an intersection of an ulcer candidate. |
| Sr; | Average saturation-related value of pixels pertaining to an intersection of an ulcer candidate. |
| Vr; | Average intensity-related value of pixels pertaining to an intersection of an ulcer candidate. |
| dH; | Difference between a chroma-related value of pixels pertaining to a center of an ulcer candidate and chroma-related value of pixels pertaining to an intersection of an ulcer candidate, e.g. Hc – Hr; the average H value of pixels pertaining to a center of an ulcer candidate minus the average H value of pixels pertaining to an intersection of an ulcer candidate. |

TABLE 1-continued

Sample parameters for property vectors or lists.

| Abbreviation | Description |
| --- | --- |
| dS; | Difference between a saturation-related value of pixels pertaining to a center of an ulcer candidate and saturation-related value of pixels pertaining to an intersection of an ulcer candidate, e.g. Sc – Sr; the average S value of pixels pertaining to a center of an ulcer candidate minus the average S value of pixels pertaining to an intersection of an ulcer candidate. |
| dV; | Difference between an intensity-related value of pixels pertaining to a center of an ulcer candidate and intensity-related value of pixels pertaining to an intersection of an ulcer candidate, e.g. Vc – Vr; the average V value of pixels pertaining to a center of an ulcer candidate minus the average V value of pixels pertaining to an intersection of an ulcer candidate. |
| dH/Hc; | Ratio of the difference between a chroma-related value of pixels pertaining to a center of an ulcer candidate and chroma-related value of pixels pertaining to an intersection of an ulcer candidate to an average chroma-related value of pixels pertaining to a center of an ulcer candidate, e.g. the average H value of pixels pertaining to a center of an ulcer candidate minus the average H value of pixels pertaining to an intersection of an ulcer candidate, divided by the average H value of pixels pertaining to a center of an ulcer candidate. |
| dS/Sc; | Ratio of the difference between a saturation-related value of pixels pertaining to a center of an ulcer candidate and saturation-related value of pixels pertaining to an intersection of an ulcer candidate, to an average saturation-related value of pixels pertaining to a center of an ulcer candidate, e.g., an average S value of pixels pertaining to a center of an ulcer candidate minus the average S value of pixels pertaining to an intersection of an ulcer candidate divided by the average S value of pixels pertaining to a center of an ulcer candidate. |
| dV/Vc; | Ratio of the difference between an intensity-related value of pixels pertaining to a center of an ulcer candidate and intensity-related value of pixels pertaining to an intersection of an ulcer candidate, to an average intensity-related value of pixels pertaining to a center of an ulcer candidate, e.g. the average V value of pixels pertaining to a center of an ulcer candidate minus the average V value of pixels pertaining to a ring of an ulcer candidate divided by the average V value of pixels pertaining to an intersection of an ulcer candidate. |
| centerArea; | The size of the center of the ulcer candidate, measured, for example, in pixels. |
| perimeterVal^2/ centerArea; | Square of the circumference of the center of the ulcer candidate divided by the size of the ulcer center. |
| intersArea; | The size of the intersection area, e.g. in pixels. |
| haloArea; | The total size of the area included in the ring of the ulcer candidate. |
| intersArea/ haloArea; | The size of the intersection area divided by the total size of the ring of the ulcer candidate. |
| largestContribution; | The largest part of the corresponding intersection area that pertains to a single ulcer halo candidate. Also referred to as the largest contribution. |
| largestContribution/ haloArea; | The largest contribution divided by the total size of the area included in the ring. |
| sizeOfMainContributor; | The size of the ulcer halo candidate which gives the largest contribution. |

Other parameters or combinations (e.g. linear or nonlinear) of parameters may be used, and the parameters may be based on one or more color space representations. When used herein, an "average" value may be calculated, for example, as an arithmetic mean, median, geometric mean, harmonic mean, mode, weighted mean, etc. In operation 390 a trained classifier, for example a trained classifier such as trained classifiers 215, 225 and 235, may be employed, used or executed to generate a rating or grade indicative of the probability that the ulcer candidate is an ulcer based on the property vector. The trained classifier may be a supervised learning classifier such as a neural network classifier, a Fisher linear discriminant classifier, a sparse network of Winnows classifier, a decision tree classifier, a Bayes classifier, a support vector machine, or an AdaBoost classifier. The classifier may be trained in advance using a set of positive examples and a set of negative examples, as will be discussed herein. Alternatively, unsupervised learning classifiers may be used.

In operation 395 a rating or grade indicative of the highest probability that an ulcer candidate or region possibly being an image of an ulcer is an ulcer may be calculated or selected for each image. Thus, each ulcer recognition module may give a single grade for each image, the single grade indicative of the probability that the image includes an ulcer. For example, the single grade may be indicative of the probability that the image includes an ulcer of a type that the ulcer recognition module was designed to detect. If no ulcer candidate reaches operation 395 the image may receive a grade indicative of the lowest possible probability that that image includes an ulcer of a type that the ulcer recognition module was designed to detect. Operation 395 may be optional. Alternatively, a grade may be given by the ulcer recognition module to each ulcer candidate that was not filtered out. Ulcer candidates may be noted or marked, for example, by their location in the image (e.g., by altering or adding metadata to image data).

Figure 5:
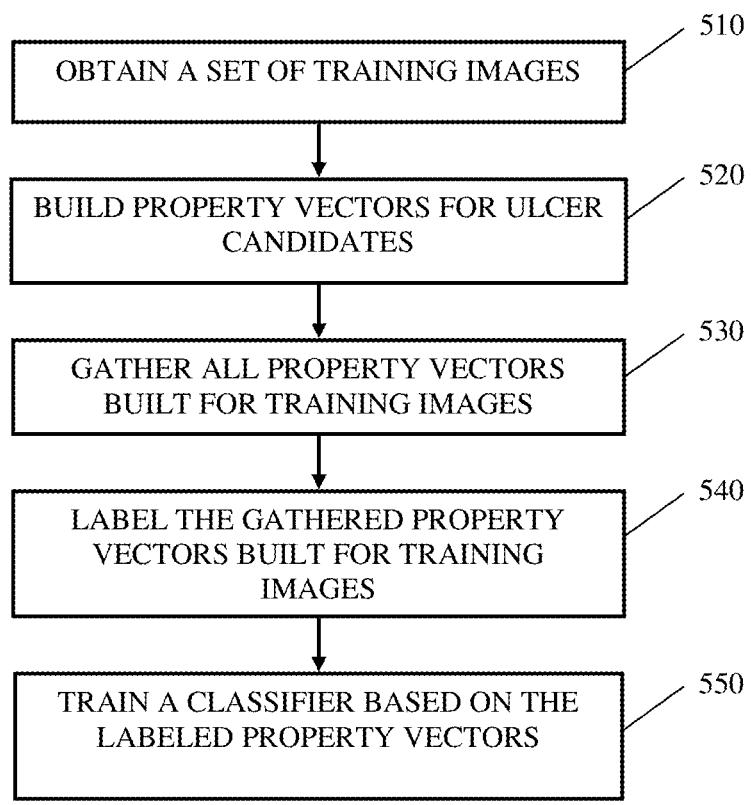
FIG. 5 is a flowchart illustration of a method for training a classifier according to embodiments of the present invention.

Reference is now made to FIG. 5 which is a flowchart of a method for training a classifier according to embodiments of the present invention. Each trained classifier of each ulcer recognition module, for example such as trained classifiers 215, 225 and 235, may be trained separately using the method presented in FIG. 5 with the same or different set of training images. Classifiers 215, 225 and 235 may be trained in advance, for example, in a training session. According to embodiments of the present invention, a set of training images may be obtained in operation 510. For example, the set of training images may include images labeled, for example, by a health professional as including ulcers, and images labeled, for example, by a health professional as not including ulcers. The health professional may also label the location of the ulcers found in the positive examples. In operation 520, a plurality of property vectors may be built for ulcer candidates or regions possibly portraying or depicting an image of an ulcer found in the training images. Ulcer candidates may be found and property vectors may be built as described in operations 310 to 380 presented in FIG. 3, using the same thresholds, ranges and parameters. In operation 530, substantially all property vectors are gathered. In operation 540 the gathered property vectors may be labeled as true positive and false positive, to create a set of positive examples and a set of negative examples. The labeling of property vectors may be based on, for example, labeling of ulcers found in the set of training images made by the health professional. In operation 550 the classifier for an ulcer recognition module may be trained based on the labeled property vectors. Training of the classifier may be performed according to any suitable training method applicable for the selected classifier, as known in the art.

Figure 6:
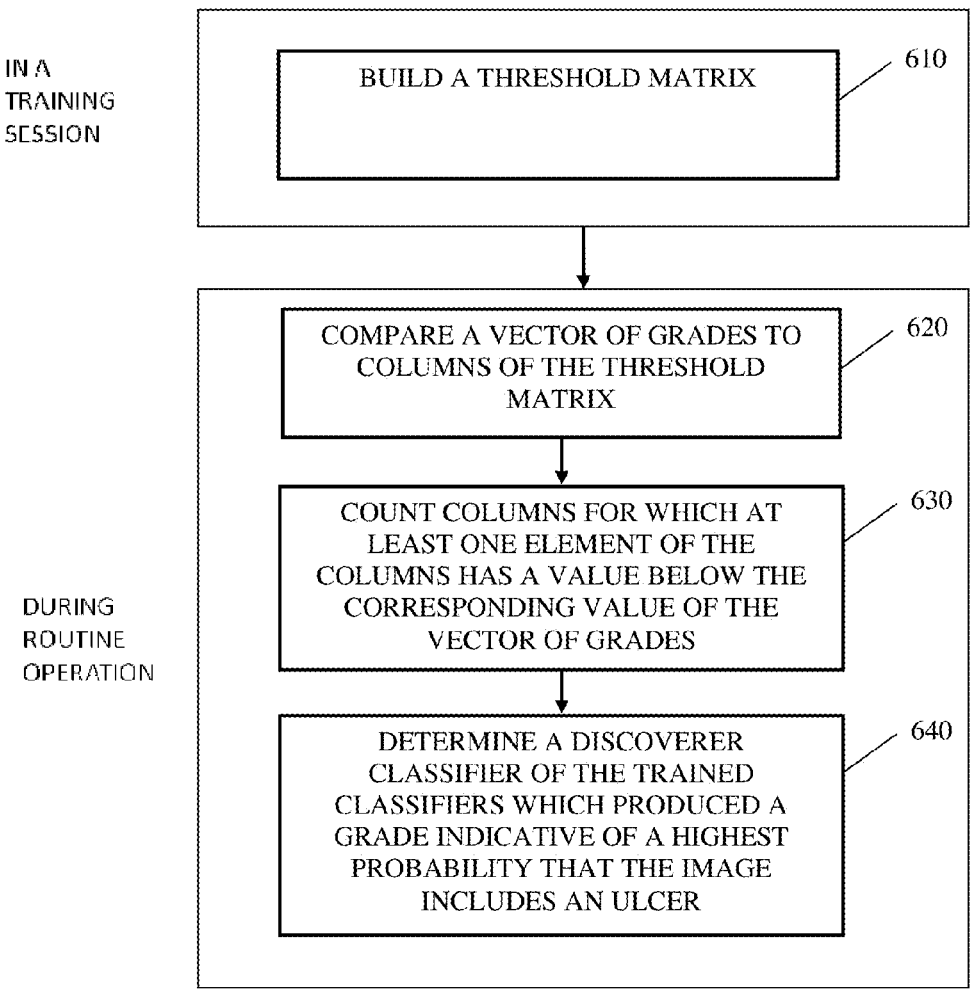
FIG. 6 is a flowchart illustration of a method for combining grades generated by a plurality of ulcer detectors according to embodiments of the present invention.

Reference is now made to FIG. 6 which is a flowchart illustration of a threshold matrix method for integrating or combining ratings or grades generated by a plurality of ulcer recognition modules according to embodiments of the present invention. For example, the method for combining grades presented in FIG. 6 may be performed by integrator 240.

According to embodiments of the present invention, a threshold matrix may be built or calculated in operation 610. Typically, the number of the rows of the threshold matrix equals the number of different ulcer recognition modules. The values of the threshold matrix may be monotonically decreasing along each row. For example, the threshold matrix may be built as described herein. A training set of examples of vector of grades may be generated or obtained, where the training set includes a set of positive examples, e.g. grade vectors built using images that include at least one ulcer, and a set of negative examples, e.g. grade vectors built using images that include no ulcers. An i-th element of a grading vector may, for example, be the grade given to the image or ulcer candidate by i-th ulcer recognition module. The threshold matrix may be initiated as a single-column matrix with all its entries set to infinity. Additional columns may be added in an iterative process. In each iteration, a set of candidate new columns may be calculated or generated. Each candidate new column may be generated by decreasing a single value, while leaving other values unchanged in comparison to a previously added column, such that at least one additional positive example will be counted. An example is counted if at least one element of the candidate new column has a value below the corresponding value of the example. For each of the candidate new columns, a ratio between a number of additional positive examples that will be counted and a number of additional negative examples that will be counted may be calculated. The candidate new column for which the ratio was maximal with relation to other candidate new columns may be added to the threshold matrix. New columns may be added until a stopping criterion has been met. The stopping criterion may be, for example, that all positive examples are counted. Alternatively, other suitable stopping criterions may be used. The threshold matrix may be further processed to reduce the number of columns, for example, by deleting the first added columns. The threshold matrix may be prepared in advance, stored, for example, in storage unit 19, and used during routine operation.

In operation 620 a vector of ratings or grades calculated or generated during routine operation for image captured by, for example, imaging device 40 may be compared to columns of the threshold matrix. Each vector of grades may include grades given by ulcer recognition modules such as ulcer recognition modules 210, 220 and 230, to a whole image. In operation 630, columns of the threshold matrix for which at least one element of the columns has a value below the corresponding value of the vector of grades may be counted. The single indication of the probability that the image includes an ulcer may relate to the number of columns counted. For example, the single indication of the probability that the image includes an ulcer, may equal the number of columns counted. In optional operation 640 a discoverer classifier may be determined. The discoverer classifier may be one of trained classifiers 215, 225 and 235 which produced a grade indicative of a highest probability that the image includes an ulcer, e.g. an ulcer of a certain type. Determining the discoverer classifier may be done by determining the first column to be counted when counting columns, and determining an element of this column that is different from the corresponding element of the previous column. Due to the iterative procedure of building or creating the threshold matrix described hereinabove, only one such element may exist and may indicate the discoverer classifier. Also due to the structure of the built threshold matrix, e.g. the values of the threshold matrix may be monotonically decreasing along each row, and only one value changes from column to column, the grade given to the image by the discoverer classifier may lay in the interval defined by the two elements of the threshold matrix.

Figure 7:
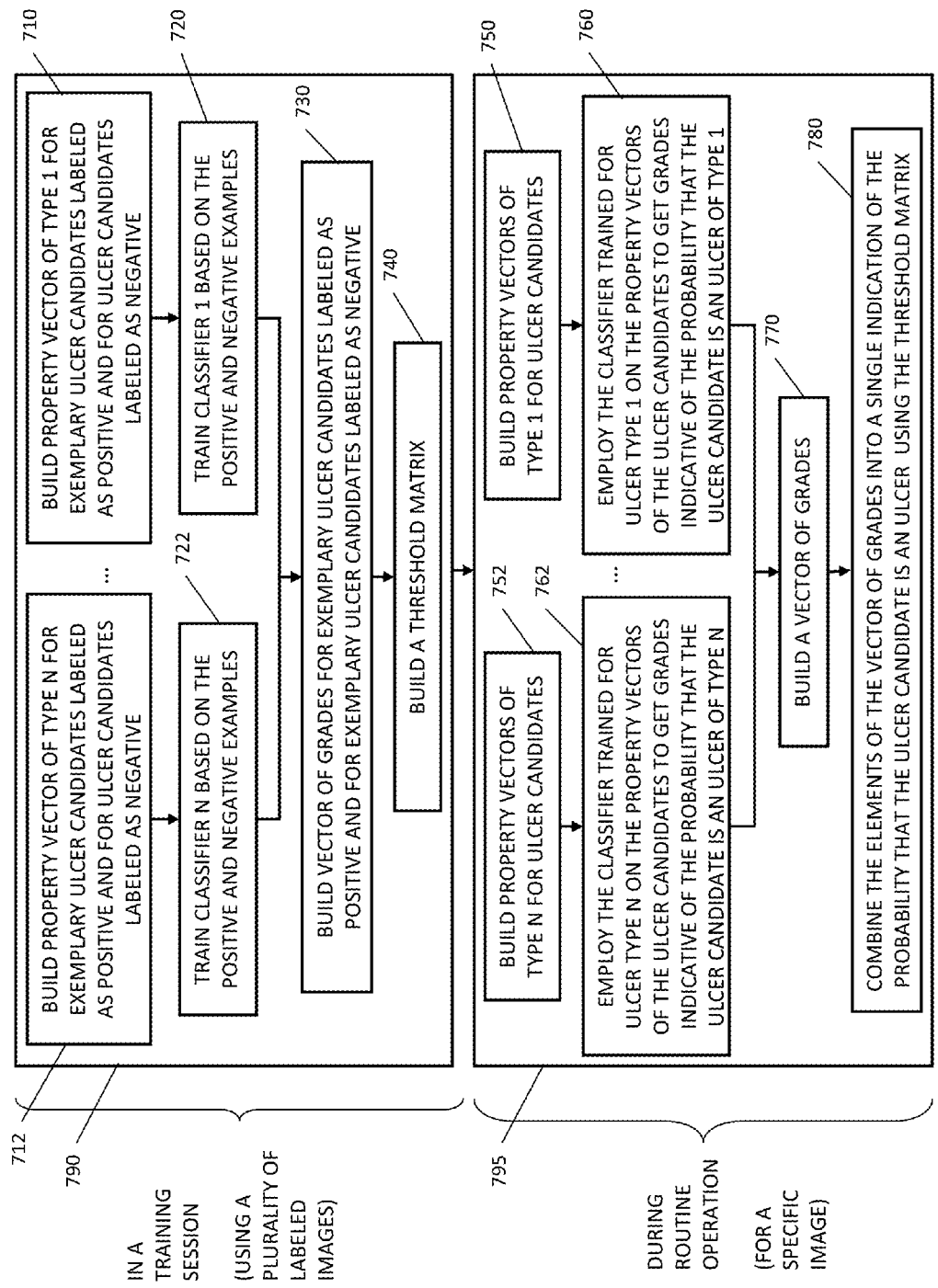
FIG. 7 is a flowchart illustration of a method for ulcer detection according to embodiments of the present invention.
Figure 8C:
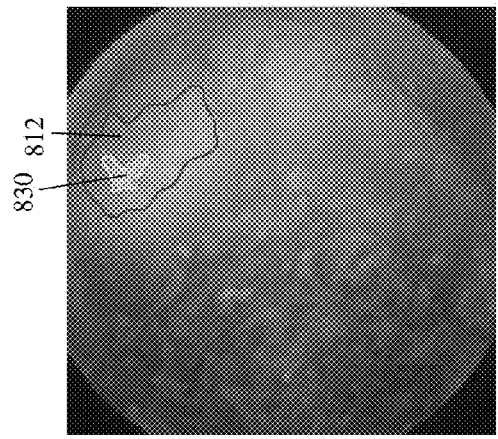
FIGS. 8A-8F present exemplary ulcers as seen in images of the GI tract taken by an in vivo imaging device such as imaging device.
Figure 8F:
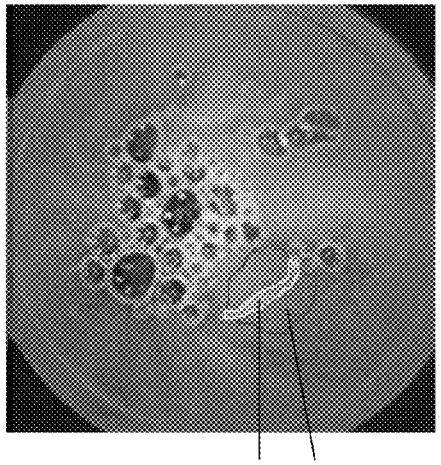
Figure 8B:
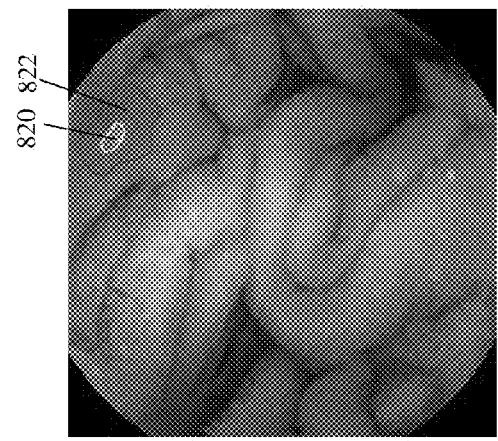
Figure 8E:
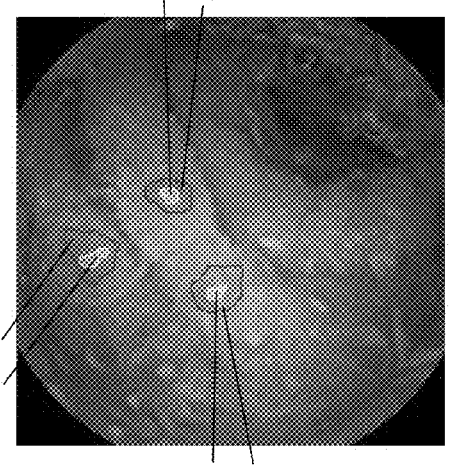
Figure 8A:
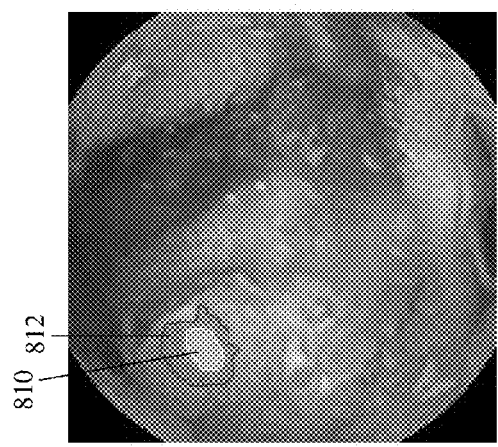
Figure 8D:
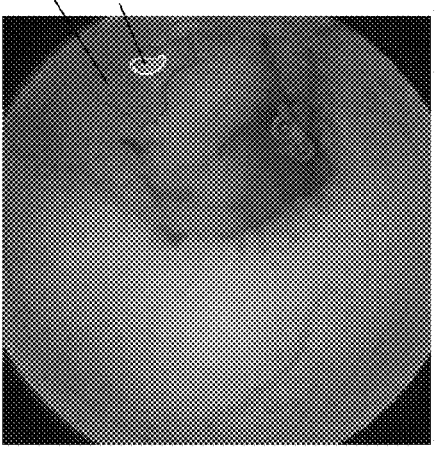

Reference is now made to FIG. 7 which is a flowchart of a method for ulcer detection according to embodiments of the present invention. For example, some or all of the operations for ulcer detection presented in FIG. 7 may be performed by ulcer detector 22. for example, operation 795 may be performed by ulcer detector 22.

Block 790 may include operations performed in a training session, using a set labeled images, while block 795 may include operations that may be performed during routine operation using the results of the training session on images of the GI tract, for example images captured in vivo by imaging device 40.

In operations 710 and 712, a plurality of property vectors may be calculated or built, for example, by operations 310 to 380 of FIG. 3, for exemplary ulcer candidates or a regions possibly being an image of an ulcer labeled as positive and for exemplary ulcer candidates labeled as negative. In operations 720 and 722 a plurality of classifiers may be trained, each with corresponding property vectors, labeled as positive and negative. Classifier for a specific ulcer recognition module may be trained using property vectors created and labeled for this specific module, i.e. the vectors created by operations 310-380 with parameters that correspond to this module. Note, that labeling required here may be per vector, in this case an image with an ulcer may produce vectors that will be labeled as positive as well as vectors that will be labeled as negative. In operation 730 an exemplary vector of grades may be generated, calculated or built using the trained classifiers for the exemplary ulcer candidates. Operations 310-395 or 310-390 may be performed for exemplary images labeled as positive and exemplary images labeled as negative. A single exemplary vector of grades may be generated or built for each exemplary image, for example, by including the highest grade given by each classifier to an exemplary ulcer candidate included in the exemplary image. If no ulcer candidates were detected, a grade indicative of the lowest probability that the exemplary image includes an ulcer may be included. Alternatively, grades of each ulcer candidate may be organized in vector of grades. In operation 740, a threshold matrix may be built based on the exemplary vectors of grades derived in operation 730.

In operations 750 and 752 property vectors of various types may be calculated or built, for example, by operations 310 to 380 of FIG. 3. Each type of property vector may correspond to a type of ulcer. In operations 760 and 762 a classifier trained to detect a certain type of ulcer, may be employed, used or executed on a property vector of the same type to obtain or generate ratings or grades indicative of the probability that the ulcer candidates are indeed ulcers of that type. Optionally, a single grade may be given by each classifier to each image, the grades indicative of the probability that the image includes an ulcer of specific type, for example, by selecting the highest grade given by each classifier to an ulcer candidates of the corresponding type included in the image. If no ulcer candidates of that type were detected, a grade indicative of the lowest probability that the image includes an ulcer of this type may be included. In operation 770 a vector of grades may be generated, calculated, built or created, either for each ulcer candidate or for each image. In operation 780 elements of the vector of grades may be combined to form or obtain a single indication of the probability that the ulcer candidate is an ulcer, or that the image includes an ulcer, using the threshold matrix.

Reference is now made to FIGS. 8A-8F, presenting exemplary ulcers as seen in images of the GI tract taken by an in vivo imaging device such as imaging device 40. Ulcer centers 810, 820, 830, 840, 850, 860, 870 and 880 are encircled by a yellow line and ulcer halos 812, 822, 832, 842, 852, 862, 872 and 882 are encircled by a red line.

Figure 9:
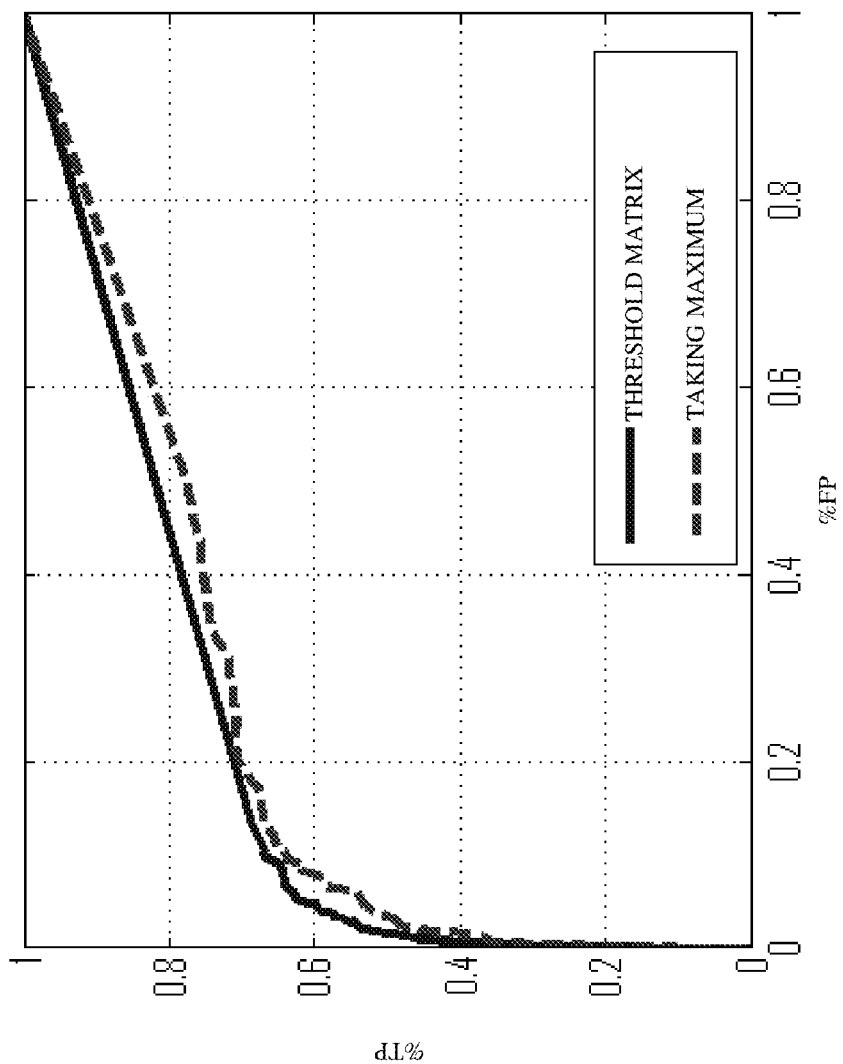
FIG. 9 presents exemplary receiver operating characteristic (ROC) curves of an ulcer detector implementing two different types of integrators.

Reference is now made to FIG. 9 presenting exemplary receiver operating characteristic (ROC) curves, also known as relative operating characteristic curves, of an ulcer detector 22 implementing two different types of integrators 240. The full line presents a ROC curve of an integrator implementing the threshold matrix method described hereinabove. The dashed line presents a ROC curve of an integrator in which ratings or grades generated by a plurality of ulcer recognition modules are combined by selecting a maximum value of the grading vector. The ROC curve presents the true positive rate (% TP), vs. false positive rate (% FP) for different values of discrimination thresholds. The term discrimination threshold refers to the value of the single indication generated by integrator 240 above which an image is considered as including an ulcer or an ulcer candidate is considered as an ulcer. It is noted that for substantially every value of discrimination threshold, the true positive rate vs. false positive rate is higher for the integrator implementing the threshold matrix method than for the integrator implementing the selection of maximum value method. Other methods may be used to combine grades, scores or ratings generated by a plurality of ulcer recognition modules which may be applied for an image.

According to embodiments of the present invention, the indication of the probability that an image includes an ulcer (e.g. an ulcer score of an image) may be used for editing a moving image stream of the GI tract. For example, images with indication of high probability (e.g., above a predetermined or user-selected threshold) that the image includes an ulcer may be presented to a health professional for further analysis. For example, these images may be presented on images monitor 18. Optionally, a visual mark may be added on the presented image to indicate where an ulcer is suspected. Other indications correlating to an indication of the probability that an ulcer candidate is an ulcer, or that an image includes an ulcer, may be displayed, for example on monitor 18, or stored, or otherwise made use of. For example, indications of images which have a high probability of containing an ulcer may be added to a summarized bar (e.g. a color bar, or another visual representation) of the image stream. Methods of generating a summarized color bar are disclosed, for example, in U.S. Pat. No. 7,215,338 to Horn et al., assigned to the common assignee of the present application and incorporated by reference in its entirety.

Thumbnail or reduced-size images may be created, for example automatically by the processor, for images that received a high probability of including an ulcer, and may be to a user as suspected ulcers detected in the images. In some embodiments, the ulcer score may be calculated for a set of images (e.g. for all images of the image stream), and an edited image stream may be generated based on, inter alia, the ulcer scores. Methods for editing an image stream are disclosed, for example, in U.S. Pat. No. 7,986,337 to Davidson et al., assigned to the common assignee of the present application and incorporated by reference in its entirety.

Some embodiments of the present invention may be implemented in software for execution by a processor-based system, for example, ulcer detector 22. For example, embodiments of the present invention may be implemented in code and may be stored on a storage medium having stored thereon instructions which can be used to program a system to perform the instructions. Embodiments of the invention may include an article such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein. The storage medium may include, but is not limited to, any type of disk including floppy disks, optical disks, compact disk read-only memories (CD-ROMs), rewritable compact disk (CD-RW), and magneto-optical disks, semiconductor devices such as read-only memories (ROMs), random access memories (RAMs), such as a dynamic RAM (DRAM), erasable programmable read-only memories (EPROMs), flash memories, electrically erasable programmable read-only memories (EEPROMs), magnetic or optical cards, or any type of media suitable for storing electronic instructions, including programmable storage devices. Other implementations of embodiments of the present invention may comprise dedicated, custom, custom made or off the shelf hardware, firmware or a combination thereof.

Embodiments of the present invention may be realized by a system that may include components such as, but not limited to, a plurality of central processing units (CPU) or any other suitable multi-purpose or specific processors or controllers, a plurality of input units, a plurality of output units, a plurality of memory units, and a plurality of storage units. Such system may additionally include other suitable hardware components and/or software components.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of ulcer detection in in vivo images, the method comprising:
    obtaining an in vivo image;
    finding ulcer candidates within the image by, using a computer processor to:
        mark pixels having a color within a first predetermined range as candidate pixels for ulcer centers;
        mark pixels having a color within a second predetermined range as candidate pixels for ulcer halos;
        unite a plurality of candidate pixels for ulcer centers to create ulcer center candidates;
        unite a plurality of candidate pixels for ulcer halos to create ulcer halo candidates; and
        combine ulcer halo candidates and ulcer center candidates to create ulcer candidates;
    for each ulcer candidate, using the processor to calculate a property vector comprising parameters describing properties of the ulcer candidate; and
    using the processor to employ one or more trained classifiers to generate an ulcer grade for the image using the property vector, wherein the ulcer grade is indicative of a probability that the image depicts an ulcer of specific type.

2. The method of claim 1, wherein combining the ulcer halo candidates and the ulcer center candidates to create ulcer candidates comprises, for each ulcer center candidate:
    forming a boundary around the ulcer center candidate, wherein the boundary defines a ring area between the boundary and the ulcer center candidate; and
    calculating an intersection area for the ulcer center candidate, the intersection area comprising pixels of the ulcer halo candidates that are included within the ring area.

3. The method of claim 2, wherein the boundary is formed by using a morphological opening operation followed by removing pixels of the ulcer center candidate.

4. The method of claim 1, comprising removing ulcer candidates by using screening tests selected from the list comprising:
    filtering to remove the ulcer candidates for which a size of a ring area is above a first predetermined value,
    filtering to remove the ulcer candidates for which a size of an intersection area is below a second predetermined value,
    filtering to remove the ulcer candidates for which the size of an intersection area divided by the size of a ring area is below a third predetermined value,
    filtering to remove the ulcer candidates for which square of a circumference of the ulcer center candidate divided by a size of the ulcer center candidate is above a fourth predetermined value,
    filtering to remove the ulcer candidates for which a difference between an average color of the ulcer center candidates and an average color of an intersection area is outside a third predetermined range, and
    filtering to remove the ulcer candidates for which a largest part of the ring area that pertains to a single ulcer halo candidate is above a fifth predetermined value.

5. The method of claim 4, comprising ordering the screening tests according to their computational complexity, and performing the screening tests sequentially, such that screening tests with low complexity are performed first.

6. The method of claim 1, wherein at least one property in the property vector includes one or more of:
    an average chroma-related value of pixels pertaining to the ulcer center candidate, the center candidate having an area and a circumference,
    an average saturation-related value of pixels pertaining to the ulcer center candidate,
    an average intensity-related value of pixels pertaining to the ulcer center candidate,
    an average chroma-related value of pixels pertaining to a ring area,
    an average saturation-related value of pixels pertaining to a ring area,
    an average intensity-related value of pixels pertaining to a ring area,
    the area size of the ulcer center candidate,
    the circumference of the ulcer center candidate,
    the size of an intersection area,
    a total size of halo candidates combined with the ulcer candidate,
    a largest contribution, wherein the largest contribution is a largest part of a ring area that pertains to a single ulcer halo candidate combined with the ulcer candidate, and
    a size of the ulcer halo candidate which gives the largest contribution.

7. The method of claim 1, comprising presenting an image which has an indication of a probability above a threshold that the image includes an ulcer to a health professional for further analysis.

8. The method of claim 7, comprising adding a visual mark of the ulcer candidates in the presented image.

9. The method of claim 1, comprising editing an image stream of the gastrointestinal tract using the generated ulcer grade of each image in the image stream.

10. A system for ulcer detection in in vivo images, the system comprising:
    a processor configured to:
        obtain an in vivo image,
        find ulcer candidates within the image by:
            marking pixels having a color within a first predetermined range as candidate pixels for ulcer centers;

marking pixels having a color within a second predetermined range as candidate pixels for ulcer halos;
uniting a plurality of candidate pixels for ulcer centers to create ulcer center candidates;
uniting a plurality of candidate pixels for ulcer halos to create ulcer halo candidates; and
combining ulcer halo candidates and ulcer center candidates to create ulcer candidates;
for each ulcer candidate, calculate a property vector comprising parameters describing properties of the ulcer candidate; and
employ one or more trained classifiers to generate an ulcer grade for the image using the property vector, wherein the ulcer grade is indicative of a probability that the image depicts an ulcer of specific type; and
a monitor to display images with ulcer candidates.

11. The system of claim 10, wherein the processor is further configured to combine the ulcer halo candidates and the ulcer center candidates by:
forming a boundary around the ulcer center candidate, wherein the boundary defines a ring area between the boundary and the ulcer center candidate; and
calculating an intersection area for the ulcer center candidate, the intersection area comprising pixels of the ulcer halo candidates that are included within the ring area.

12. The system of claim 11, wherein the processor is further configured to form the boundary by using a morphological opening operation followed by removing pixels of the ulcer center candidate.

13. The system of claim 10, wherein the processor is further configured to remove ulcer candidates by using screening tests selected from the list comprising:
filtering to remove the ulcer candidates for which a size of a ring area is above a first predetermined value,
filtering to remove the ulcer candidates for which a size of an intersection area is below a second predetermined value,
filtering to remove the ulcer candidates for which the size of an intersection area divided by the size of a ring area is below a third predetermined value,
filtering to remove the ulcer candidates for which square of a circumference of the ulcer center candidate divided by a size of the ulcer center candidate is above a fourth predetermined value,
filtering to remove the ulcer candidates for which a difference between an average color of the ulcer center candidates and an average color of an intersection area is outside a third predetermined range, and
filtering to remove the ulcer candidates for which a largest part of the ring area that pertains to a single ulcer halo candidate is above a fifth predetermined value.

14. The system of claim 13, wherein the processor is further configured to: order the screening tests according to their computational complexity, and perform the screening tests sequentially, such that screening tests with low complexity are performed first.

15. The system of claim 10, wherein at least one property in the property vector includes one or more of:
an average chroma-related value of pixels pertaining to the ulcer center candidate, the center candidate having an area and a circumference,
an average saturation-related value of pixels pertaining to the ulcer center candidate,
an average intensity-related value of pixels pertaining to the ulcer center candidate,
an average chroma-related value of pixels pertaining to a ring area,
an average saturation-related value of pixels pertaining to a ring area,
an average intensity-related value of pixels pertaining to a ring area,
the area size of the ulcer center candidate,
the circumference of the ulcer center candidate,
the size of an intersection area,
a total size of halo candidates combined with the ulcer candidate,
a largest contribution, wherein the largest contribution is a largest part of a ring area that pertains to a single ulcer halo candidate combined with the ulcer candidate, and
a size of the ulcer halo candidate which gives the largest contribution.

16. The system of claim 10, wherein the monitor is to display an image with an above-threshold probability that the image includes an ulcer to a health professional for further analysis.

17. The system of claim 16, wherein the processor is further configured to add a visual mark of the ulcer candidates in the displayed image.

18. The system of claim 10, wherein the processor is further configured to edit an image stream of the gastrointestinal tract based on the generated ulcer grade of each image in the image stream.

19. A method of ulcer detection in an in vivo image stream of the gastrointestinal tract, the method comprising:
obtaining an image stream comprising in vivo images;
using a computer processor to find ulcer candidates within each image by:
marking pixels having a color within a first predetermined range as candidate pixels for ulcer centers;
marking pixels having a color within a second predetermined range as candidate pixels for ulcer halos;
uniting a plurality of candidate pixels for ulcer centers to create ulcer center candidates;
uniting a plurality of candidate pixels for ulcer halos to create ulcer halo candidates; and
using the computer processor to combine ulcer halo candidates and ulcer center candidates to create ulcer candidates by forming a boundary around the ulcer center candidate, wherein the boundary defines a ring area between the boundary and the ulcer center candidate, and to calculate an intersection area for the ulcer center candidate, the intersection area comprising pixels of the ulcer halo candidates that are included within the ring area;
for each ulcer candidate, using the computer processor to calculate a property vector comprising parameters describing properties of the ulcer candidate;
using the computer processor to employ one or more trained classifiers to generate an ulcer grade for each image using the property vector, wherein the ulcer grade is indicative of a probability that the image depicts an ulcer of specific type; and
using a computer processor to edit the image stream of the gastrointestinal tract based on the generated ulcer grades of each image in the image stream.

* * * * *